United States Patent [19]

Chin et al.

[11] Patent Number: 4,976,725
[45] Date of Patent: Dec. 11, 1990

[54] DILATATION CATHETER AND CONSTANT PRESSURE SYRINGE AND METHOD OF USING THE SAME

[75] Inventors: Albert K. Chin, Palo Alto; Thomas J. Fogarty, 770 Welch Rd., Palo Alto, Calif. 94304

[73] Assignee: Thomas J. Fogarty, Palo Alto, Calif.

[21] Appl. No.: 871,461

[22] Filed: Jun. 5, 1986

[51] Int. Cl.$^5$ .......................................... A61M 29/02
[52] U.S. Cl. .................................. 606/192; 606/194; 604/97; 604/98
[58] Field of Search .......................... 128/348.1, 344; 604/97-99, 104-143, 146, 152; 606/194, 192

[56] References Cited

U.S. PATENT DOCUMENTS

| 705,251 | 7/1902 | King et al. | 604/146 |
|---|---|---|---|
| 1,541,615 | 6/1925 | Bessesen | 604/143 |
| 3,409,016 | 11/1968 | Foley | 604/98 |
| 4,526,175 | 7/1985 | Chin et al. | 128/344 |
| 4,655,749 | 4/1987 | Fischione | 128/344 |

FOREIGN PATENT DOCUMENTS

| 2024837 | 12/1971 | Fed. Rep. of Germany | 604/141 |
|---|---|---|---|
| 1791094 | 2/1978 | Fed. Rep. of Germany | 604/141 |
| 16647 | of 1911 | United Kingdom | 604/141 |

Primary Examiner—Michael H. Thaler
Attorney, Agent, or Firm—Limbach, Limbach & Sutton

[57] ABSTRACT

In a dilatation catheter and constant pressure syringe, a pressurized compressible medium is used to maintain pressure on a non-compressible medium. Pressure is applied to a compressible medium in a first chamber, in turn applying pressure to a non-compressible medium in a second chamber. The use of appropriate quantities of each medium produces a nearly constant pressure as the incompressible medium is ejected from the syringe.

6 Claims, 1 Drawing Sheet

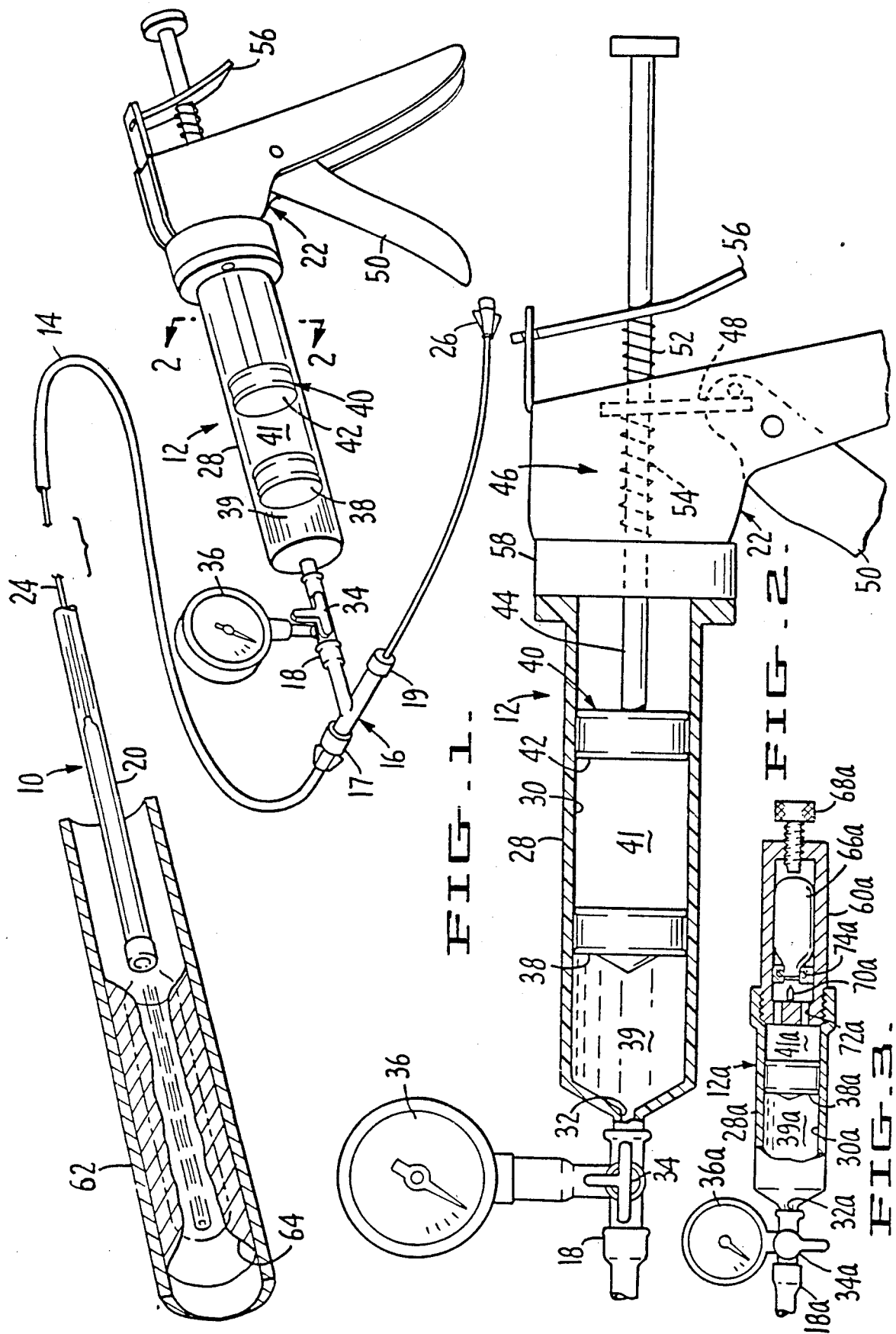

DILATATION CATHETER AND CONSTANT PRESSURE SYRINGE AND METHOD OF USING THE SAME

BACKGROUND OF THE INVENTION (1) Field of the Invention

The field of the invention is in the broad sense medical syringes. More specifically, the invention relates to dilatation catheters of the inversion-eversion type and an actuator therefor characterized by the use of a compressible fluid to maintain nearly constant pressure on an incompressible fluid which fills the catheter while the balloon element of the catheter is everted and inflated.

(2) Description of the Prior Art

We are not aware of any device which uses a compressible fluid in order to maintain pressure on the incompressible fluid that fills the catheter.

A Double Lumen Dilatation Catheter having a catheter portion of the type incorporated in the present invention is shown in Chin, et al. U.S. Pat. No. 4,526,175. An alternative method of inflating a catheter balloon by means of a Combined Large and Small Bore Syringe is shown in Chin, U.S. Pat. No. 4,476,866.

SUMMARY OF THE INVENTION

The gist of the invention is the provision in an invert-evert dilatation catheter of actuator means comprising a means of pressurizing a compressible fluid, such as air, which then applies pressure to an incompressible fluid, such as water, which fills the catheter. The inclusion of the compressible fluid provides two important advantages, first in allowing for a larger reservoir of the incompressible fluid to be kept under pressure than in previous devices, typically a syringe, so that longer catheters may be inflated without refilling the syringe. Second, prior inflation schemes usually require two operators, one to apply pressure and the other to extend the balloon portion of the catheter. The present invention enables one person to easily perform both functions.

The catheter portion of the invention is that shown in Chin, et al., U.S. Pat. No. 4,526,175. The syringe portion is characterized by a cylinder divided into two chambers by a movable barrier. One chamber is filled with an incompressible fluid and communicates with the catheter with which the syringe is used. The other chamber is filled with a compressible fluid which is maintained under pressure.

BRIEF DESCRIPTION OF THE DRAWINGS

FIG. 1 is a view in perspective of the syringe of the invention attached to a dilatation catheter disposed in treating relationship to an occluded blood vessel.

FIG. 2 is a sectional-elevational view of the syringe portion of the apparatus taken on the plane designated by line 2—2 in FIG. 1.

FIG. 3 is an elevational view of a further embodiment of the syringe portion of the apparatus, with parts broken away and shown in section.

DESCRIPTION OF THE PREFERRED EMBODIMENT

Referring to FIGS. 1 and 2, the device of the invention is comprised of a dilatation catheter portion indicated generally at 10 and a syringe portion indicated generally at 12.

The catheter portion 10 is comprised of an outer catheter 14, a Y-shaped catheter housing 16 having one leg 17 secured in sealed fluid communication with the proximal end of the catheter 14, a balloon inflation port 18 disposed in another leg and a third leg 19 aligned with the leg 17. An annular, elongated balloon 20 is connected to the distal end of the outer catheter 14. An inner catheter 24 is sealingly secured to the balloon 20 to provide a passageway therethrough and extends through the housing 16 and a seal (not illustrated) disposed within the leg 19. A fitting 26 is connected to the proximal end of the catheter 24.

The outer catheter 14 and the inner catheter 24 are made of a plastic material that is flexible but non-collapsing under pressure. The balloon 20 is made of a flexible essentially non-elastomeric material, such as polyethylene. The inner catheter 24 and the balloon 20 may be constructed in a single piece, or they may be separate pieces joined together by adhesive or adhesive and suture winding.

The syringe portion 12 comprises a housing 28 mounted on a handle 22 and having defined therein a cylindrical passageway 30 terminating in a distal outlet passage 32 of reduced size, the latter being in communication with the catheter 14 through a valve 34 and pressure gauge 36. The valve 34 is attached to inflation port 18 in housing 16. A first, free-moving, flexible land piston member 38 is slidably disposed within cylinder tube 28, defining a chamber 39. A second piston member 40 comprised of flexible land 42 and shaft 44 is slidably disposed within cylinder 26 with first piston member 38 located between second piston member 40 and outlet passage 32, thus defining a second chamber 41. Shaft 44 extends through a friction ratchet mechanism 46 of the type commonly used in caulking guns. The mechanism 46 is comprised of a gripping plate 48 connected to a trigger 50, a release lever 56, a first spring 52 on shaft 44 between gripper plate 48 and release lever 56, and a second spring 54 on shaft 44 between gripping plate 48 and a stop portion 58 of handle 22.

In operation, the catheter 10 is positioned in a blood vessel 62 near an occlusion of arteriosclerotic material 64 which is desired to be cleared. The volume between the outer catheter 14 and the inner catheter 24 is filled with an incompressible fluid, such as water, as is the distal chamber 39 in the syringe 12 formed between piston member 38 and the outlet passage 32. Preferably, the bore of passageway 30 is of a sufficiently large cross-section that the volume of fluid in said distal chamber 39 exceeds the volume of the balloon 20 in its fully everted or extended position.

The second chamber 41 in the syringe, that between pistons 38 and 40, is then filled with a compressible fluid, such as air. With the valve 34 in its closed position, pressure is applied to the second piston 40 by squeezing the trigger 50 and thus advancing the shaft 44 by the friction ratchet mechanism. This compresses the compressible fluid in the second chamber 41 and thus increases the pressure on the incompressible fluid in the distal chamber 39. A pressure of approximately 75 psi is desired, but any pressure between 50 and 100 psi will work reasonably well. The valve 34 is then turned to its open position, thus pressurizing the fluid in the outer catheter 14.

The balloon 20 is extended by feeding the inner catheter 24 into the housing 16 while the fluid in the outer catheter 14 is pressurized. This functions to evert the balloon 20 from the catheter 14 in an inflated condition. Any desired length of the balloon 20 may be everted this way. As this is done, the incompressible fluid in the distal chamber 39 of the syringe 28 flows into the outer catheter 14 to fill the space created by the dilation of the balloon 20. The volume of the chamber 39 correspondingly shrinks, and the first piston 38 moves toward the distal end of the syringe housing 28. The volume of the second chamber 41 thus increases and the pressure on the compressible fluid drops. The balloon 20 may be as long as 30 to 40 cm in length, with a volume of up 25 cc or more.

If sufficient incompressible fluid is contained in the distal chamber 39 of the syringe, and a sufficient quantity of the compressible fluid is contained in the second chamber 41, the extrusion of the balloon 20 and resulting expansion of the second chamber 41 will not decrease the pressure below the level necessary for full inflation of the balloon. It has been found that a syringe with a total volume of approximately 60 cc and the pressure of 75 psi will produce satisfactory results with a balloon of the above size. This also allows a single operator to sequentially perform both operations, i.e., pressuring the catheter 14 and then everting and inflating the balloon 20, rather than requiring two persons as is commonly done at present.

After the balloon 20 is inflated to dilate the occlusion 64, the release lever 56 is pushed to release the shaft 44 and relieve the pressure on the fluids. The balloon 20 may then be inverted within the distal end of the catheter 14 by pulling on the portion of the inner catheter 24 extending past the housing 16 to draw the catheter 24 through the housing.

The through lumen in the inner catheter 24 provides a passageway from the fitting 26 to the distal end of the balloon 20 when it is everted or to the distal end of the outer catheter 14 when the balloon is inverted. This passageway allows the catheter to be inserted by means of a guide wire in a manner to which angiographers are accustomed. It also permits materials to be injected into the vessel 62 at the distal tip of the catheter, and pressures at the distal end of the catheter or balloon to be monitored proximally.

FIG. 3 shows an alternative embodiment of the syringe portion of the apparatus, where the second piston member 42 and ratchet mechanism 46 has been replaced by a source of pressurized gas, such as a cartridge of carbon dioxide illustrated here. The syringe portion of the FIG. 3 embodiment is designated 12a. The elements of the FIG. 3 embodiment corresponding to those of the previous embodiment are designated by like numerals followed by the letter "a", as follows: 18a, 28a, 30a, 32a, 34a, 36a, 38a, 39a and 41a.

The proximal end of the housing 28a is threaded to match a second housing 60a, open on one side, which receives a cartridge 66a of compressed gas, such as carbon dioxide. A thumbscrew 68a pushes the cartridge 66a into a pin 70a that punctures the end of the cartridge 66a, releasing the gas into the housing 28a via holes 72a in the end of housing 60a. A seal 74a surrounds the end of the cartridge 66a and prevents the gas from escaping in any other direction.

In this embodiment the distal chamber 39a in the housing 28a and the outer catheter 14 are filled with water. A gas cartridge 66a is inserted into housing 60a and thumbscrew 68a is tightened, causing pin 70a to puncture the cartridge 66a and releasing pressurized gas into the proximal chamber 41a of housing 28a. This creates pressure upon the water in the syringe in the first embodiment described and catheter, and the balloon 20 may then be extended as above. To reinvert the balloon, the thumbscrew is loosened; the remaining pressure in the cartridge 66a will unseat the cartridge 66a and release the remaining gas, or the cartridge 66a may be unseated by hand. The cartridge may then be removed through the open side of housing 60a. The threads on the housings 28a and 60a allow the housings to be separated so that the piston 38a may be removed in preparation for the next use. Alternatively, the entire housing 28a may be replaced.

Conclusion

From the foregoing description it is believed apparent that the present invention provides an improved syringe for maintaining a substantially constant pressure on a balloon catheter, without the necessity of constantly manually pressurizing the syringe as the balloon is inflated. It should be understood, however, that the invention is not intended to be limited to the specific embodiments described, but rather is defined by the accompanying claims.

What is claimed is:

1. In combination, a dilatation catheter comprising:
    a catheter portion comprising an elongated flexible tubular outer catheter, an invertible-eversible dilatation balloon having its distal end in secured relationship to and received within the distal end of said outer catheter, an elongated flexible tubular inner catheter extending along said outer catheter in generally spaced relation thereto, said inner catheter having its distal end attached in sealed communicating relation with the proximal end of said balloon to provide a passage through the balloon, and having an open-ended, unobstructed tubular throughbore to thereby provide said catheter with a permanently open central lumen whereby said dilatation catheter may be readily guided for emplacement by a pre-positioned guide wire; and
    a syringe portion comprising a cylinder having a distal outlet end in communication with the proximal end of said outer catheter, barrier means slidably mounted in the cylinder, a compressible fluid on the opposite side of said barrier means from the distal outlet end, and means for applying pressure to said compressible fluid.

2. The dilatation catheter of claim 1 wherein the means for applying pressure to the compressible fluid further comprises a pressurized tank of said compressible fluid having an outlet in communication with the proximal end of the cylinder.

3. The dilatation catheter of claim 1 wherein the means for applying pressure to the compressible fluid is adapted to apply selective and incremental increases in pressure.

4. The dilatation catheter of claim 3 wherein the means for applying pressure to the compressible fluid further comprises:
    a second barrier means slidably mounted in the cylinder between the first barrier means and the proximal end of the cylinder such that a chamber is defined between the two barrier means and the compressible fluid is contained within the said chamber; and a releasable means connected to said second barrier means to selectively lock said barrier in pressure imparting relationship to the compressible fluid.

5. A method of everting and inflating an invertible-eversible balloon element of a dilatation catheter from a position within the lumen of the catheter body comprising the following steps:

disposing an incompressible fluid in the catheter body;

applying generally constant pressure to the incompressible fluid by means of a compressed body of compressible fluid so as to subject the lumen to pressure by means of the incompressible fluid; and extruding the balloon from the inverted position by applying axial force thereto simultaneously with the application of the pressurized fluid to the balloon by the incompressible fluid in the catheter.

6. The method of claim 5 wherein the means of applying pressure to the incompressible fluid further includes:

providing a syringe which includes a cylinder with a plunger slidably mounted therein, and having a distal outlet end;

coupling said distal outlet end of said syringe with the proximal inlet end of the dilatation catheter;

disposing in the syringe an additional quantity of the same incompressible fluid as in the catheter body; and applying generally constant pressure to the plunger by means of the compressed body of compressible fluid.

* * * * *